US010667748B2

(12) United States Patent
Brand et al.

(10) Patent No.: US 10,667,748 B2
(45) Date of Patent: Jun. 2, 2020

(54) CONTROLLING PRESSURE DURING ENHANCED COUGH FLOW

(71) Applicant: KONINKLIJKE PHILIPS N.V., Eindhoven (NL)

(72) Inventors: Maarten Leonardus Christian Brand, Murrysville, PA (US); Michael Edward Colbaugh, Level Green, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 438 days.

(21) Appl. No.: 15/522,083

(22) PCT Filed: Oct. 15, 2015

(86) PCT No.: PCT/IB2015/057909
§ 371 (c)(1),
(2) Date: Apr. 26, 2017

(87) PCT Pub. No.: WO2016/067147
PCT Pub. Date: May 6, 2016

(65) Prior Publication Data
US 2017/0325735 A1 Nov. 16, 2017

Related U.S. Application Data

(60) Provisional application No. 62/073,487, filed on Oct. 31, 2014.

(51) Int. Cl.
A61B 5/00 (2006.01)
A61B 5/08 (2006.01)
(Continued)

(52) U.S. Cl.
CPC ............ *A61B 5/4836* (2013.01); *A61B 5/087* (2013.01); *A61B 5/0823* (2013.01); *A61B 5/091* (2013.01);
(Continued)

(58) Field of Classification Search
CPC .............. A61M 16/00; A61M 16/0003; A61M 16/0006; A61M 16/0057; A61M 16/0066;
(Continued)

(56) References Cited

U.S. PATENT DOCUMENTS 3,993,059 A * 11/1976 Sjostrand .............. A61M 16/00
128/205.13
5,345,930 A 9/1994 Cardinal
(Continued)

FOREIGN PATENT DOCUMENTS

CN 101337101 A 1/2009
CN 101642598 A 2/2010
(Continued)

OTHER PUBLICATIONS

Smith J. et al., "Cough and its Importance in COPD", International Journal of COPD 2006:1(3) 305-314 © 2006 Dove Medical Press Limited.

*Primary Examiner* — Joseph D. Boecker

(57) ABSTRACT

A system and method configured to control pressure during enhanced cough flow of a subject are provided. A pressure regulator is operated such that during an individual exhalation of the subject, the pressure regulator is toggled between a first mode in which a subject interface is closed such that substantially no gas is communicated with the airway of the subject there through and a second mode in which the subject interface is opened to cause a series of exsufflation events for the individual exhalation of the subject. The pressure relief valve is associated with the subject interface and configured to open and release gas out of the subject interface, responsive to pressure within the subject interface exceeding a predetermined threshold value so as to maintain the pressure within the subject interface within a predetermined pressure range during the enhanced cough flow.

16 Claims, 4 Drawing Sheets

(51) Int. Cl.
*A61M 16/20* (2006.01)
*A61B 5/091* (2006.01)
*A61B 5/087* (2006.01)
*A61M 16/00* (2006.01)

(52) U.S. Cl.
CPC ...... *A61M 16/0069* (2014.02); *A61M 16/024* (2017.08); *A61M 16/202* (2014.02); *A61M 16/209* (2014.02); *A61M 16/208* (2013.01); *A61M 2016/0027* (2013.01); *A61M 2205/3334* (2013.01); *A61M 2205/3365* (2013.01); *A61M 2205/50* (2013.01); *A61M 2205/502* (2013.01); *A61M 2230/40* (2013.01)

(58) Field of Classification Search
CPC .. A61M 16/022; A61M 16/024; A61M 16/20; A61M 16/201; A61M 16/202; A61M 16/205; A61M 16/208; A61M 16/209; A61M 2016/0027; A61M 2205/3334; A61M 2205/3365; A61M 2205/50; A61M 2205/502; A61B 5/087; A61B 5/091; A61B 5/4836
See application file for complete search history.

(56) References Cited

U.S. PATENT DOCUMENTS

| | | |
|---|---|---|
| 5,957,130 A | 9/1999 | Krahbichler et al. |
| 6,615,831 B1 | 9/2003 | Tuitt |
| 8,360,061 B2 | 1/2013 | Brown |
| 10,300,239 B2 | 5/2019 | Brand et al. |
| 2003/0192545 A1 | 10/2003 | Tuitt |
| 2004/0107967 A1 | 6/2004 | Flodin |
| 2008/0000477 A1 | 1/2008 | Huster |
| 2012/0111329 A1* | 5/2012 | Brand .................... A61H 23/00 128/204.23 |
| 2013/0102916 A1* | 4/2013 | Colbaugh ......... A61M 16/0816 600/533 |
| 2013/0276789 A1* | 10/2013 | Garde ............... A61M 16/0066 128/204.23 |
| 2014/0116441 A1* | 5/2014 | McDaniel ......... A61M 16/0051 128/204.23 |
| 2014/0144445 A1* | 5/2014 | Bowditch ......... A61M 16/0683 128/204.23 |
| 2014/0150801 A1 | 6/2014 | Rusher |
| 2014/0373844 A1* | 12/2014 | Brand ................ A61M 16/024 128/204.22 |

FOREIGN PATENT DOCUMENTS

| | | |
|---|---|---|
| CN | 203663191 U | 6/2014 |
| DE | 3907082 A1 | 2/1990 |
| KR | 20100000636 A | 1/2010 |
| WO | WO2011058470 A1 | 5/2011 |
| WO | WO2013001398 A1 | 1/2013 |
| WO | WO2013110861 A1 | 8/2013 |
| WO | WO2014135997 A1 | 9/2014 |

* cited by examiner

CONTROLLING PRESSURE DURING ENHANCED COUGH FLOW

CROSS-REFERENCE TO RELATED APPLICATIONS

This patent application claims the priority benefit under 35 U.S.C. § 371 of international patent application no. PCT/IB2015/057909, filed Oct. 15, 2015, which claims the priority benefit under 35 U.S.C. § 119(e) of U.S. Provisional Application No. 62/073,487 filed on Oct. 31, 2014, the contents of which are herein incorporated by reference.

BACKGROUND OF THE INVENTION

1. Field of the Invention

The present disclosure pertains to a method and an apparatus for controlling pressure during enhanced cough flow of a subject.

2. Description of the Related Art

Several respiratory diseases, such as Chronic Obstructive Pulmonary Disease (COPD), Asthma, Cystic Fibrosis (CF), etc., are characterized by an accumulation of fluid or viscoelastic material, i.e., mucus or secretions, in the respiratory system of a patient. An increase amount of mucus (due to hypersecretion and/or reduced ability to clear secretions from the lung) in the respiratory system is often associated with respiratory difficulties, and may lead to complete blockage of gas alveoli of the respiratory system. The clinical consequences of hypersecretion are impaired gas exchange and compromised mucus clearance, increasing bacterial colonization and associated exacerbations. Excess of secretion may be cleared through cough or expectorating phlegm from the throat.

A natural phenomenon to expel such lung mucus is coughing. Cough consists of an inspiratory phase, closure of glottis, a build-up of pressure in the lung by muscle contraction, followed by an expiratory phase at which the glottis is opened, resulting in airflows with high velocity that are intended to pick up any material residing on the airway wall and propel it upwards towards the mouth. In numerous situations, natural cough is insufficient to expectorate these secretions. For example, cough remains ineffective due to inability to generate sufficient cough flow, abnormal properties of secretions in the lung, or a combination of both. In a number of respiratory diseases, the inability to develop airflow has to do with collapse of the airways during the cough manoeuvre.

Assistance means to help a patient expectorate secretions have been developed. For example, various systems for increasing patient cough flow through mechanical insufflation and exsufflation are known. Conventional exsufflation is generally accomplished using a single exsufflation event over a single exhalation of the subject. A respiratory circuit may be pressurized by a device, after which device applies negative pressure to the airways, causing high expiratory flows. Secretions built up in the airway of the subject over time may be expelled with the gas.

Another system for increasing patient cough flow, for example, use a passive variable flow resistor aimed at generating pressure oscillations during exhalation such that a single cough is segmented into multiple mini-coughs by intermittently opening and closing of a valve positioned in the expiratory air path. For example, such a system is configured to periodically obstruct cough flow, periodically increase pressure in the airways during cough, and allow airways to remain open and cough volume to be maximized. In such a system, when the valve closes, the pressure in the lung or respiratory system may rapidly rise due to continued muscle contraction during the cough and, when the valve opens, the lung pressure may rapidly drop to near ambient pressures.

SUMMARY OF THE INVENTION

Accordingly, one or more aspects of the present disclosure relate to a system configured to control pressure during enhanced cough flow of a subject. The system includes a subject interface configured to communicate with an airway of the subject; a pressure regulator configured to selectively control flow through the subject interface, the pressure regulator operating in (i) a first mode in which the subject interface is closed such that substantially no gas is communicated with the airway of the subject therethrough, and (ii) a second mode in which the subject interface is opened to permit gas to be exhausted from the airway of the subject through the subject interface; a controller configured to operate the pressure regulator such that during an individual exhalation of the subject, the pressure regulator is toggled between the first mode and the second mode to cause a series of exsufflation events for the individual exhalation of the subject; and a pressure relief valve associated with the subject interface and configured to open and release gas out of the subject interface, responsive to pressure within the subject interface exceeding a predetermined threshold value so as to maintain the pressure within the subject interface within a desired range during the enhanced cough flow.

Yet another aspect of the present disclosure relates to a method for controlling pressure during enhanced cough flow of a subject. The method includes interfacing with an airway of the subject with a subject interface; operating, via a controller, a pressure regulator in a first mode in which the subject interface is closed such that substantially no gas is communicated with the airway of the subject therethrough; operating a pressure relief valve to open and release gas out of the subject interface, responsive to pressure within the subject interface exceeding a predetermined threshold value so as to maintain the pressure within the subject interface within a desired range during the enhanced cough flow; receiving information indicating pressurization of the subject interface by the subject; and exsufflating the subject with a series of exsufflation events by toggling the pressure regulator between the first mode and a second mode to create the series of exsufflation events during a single exhalation, wherein in the second mode the subject interface is opened to permit gas to be exhausted from the airway of the subject through the subject interface.

Still another aspect of present disclosure relates to a system configured to control pressure during enhanced cough flow of a subject. The system includes means for interfacing with an airway of the subject; means for selectively controlling flow through the means for interfacing, the means for selectively controlling flow operating in (i) a first mode in which the means for interfacing is closed such that substantially no gas is communicated with the airway of the subject therethrough, and (ii) a second mode in which the means for interfacing is opened to permit gas to be exhausted from the airway of the subject through the means for interfacing; means for maintaining pressure within the means for interfacing within a desired range, the means for maintaining opening and releasing gas out of the means for interfacing, responsive to the pressure within the means for interfacing exceeding a predetermined threshold value; means for receiving information indicating whether the subject has pressurized the means for interfacing; and means for controlling operation of the means for selectively controlling flow such that during an individual exhalation of the subject, the means for selectively controlling flow is toggled between the first mode and the second mode to cause a series of exsufflation events for the individual exhalation of the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
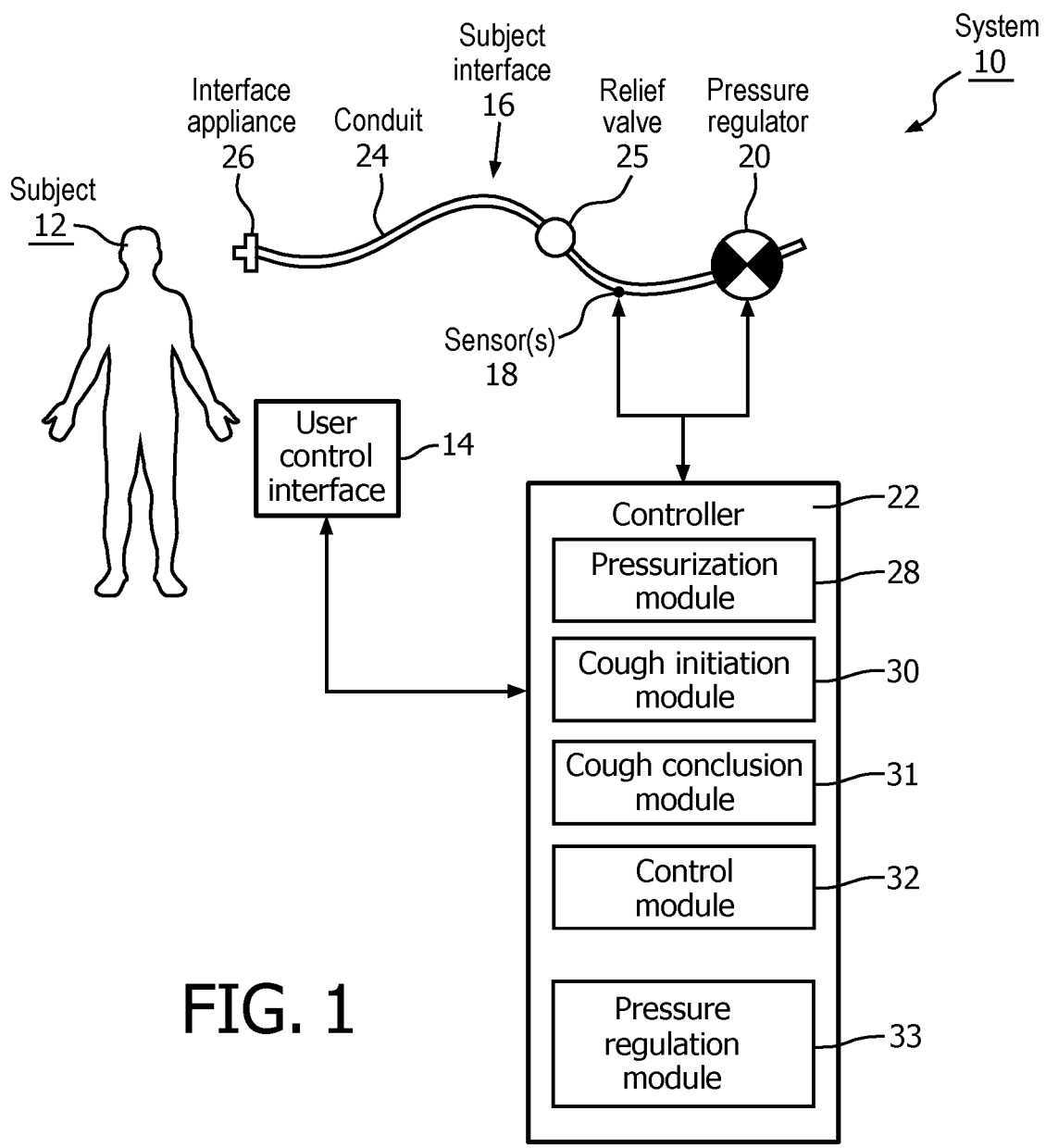
FIG. 1 shows a system configured to control pressure during enhanced cough flow of a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates an exemplary embodiment of a system 10 configured to control pressure during enhanced cough flow of a subject 12.

System 10 is configured to maintain pressure within the respiratory system of subject 12 within a desired range during the enhanced cough flow by releasing gas out from the respiratory system of subject 12 responsive to pressure within the respiratory system of subject 12 exceeding a predetermined threshold value. System 10 is configured to vent or expel gas flowing through flow path of system 10 into ambient atmosphere, as needed, so as to relieve pressure within the respiratory system of subject 12. For example, system 10 includes a secondary valve system in addition to an exsufflation valve system that is configured to cause a series of exsufflation events over an individual exhalation of subject 12. The secondary valve system allows for the pressure changes in the respiratory system of subject 12 within a predetermined range. The secondary valve system allows for controlling pressure flow in the respiratory system of subject 12 via a pressure relief valve 25 coupled to the exsufflation valve system by an air conduit. The secondary valve system is configured for regularizing internal pressure of subject 12 during the enhanced cough flow.

System 10 also enhances flow during exsufflation by, among other things, limiting airway collapse of subject 12. System 10 utilizes patient effort to pressurize system 10, and causes the series of exsufflation events over an individual exhalation of subject 12. The exsufflation events are short pulses during which air is allowed to flow out of the lungs of subject 12. Segmentation of exsufflation into a series of exsufflation events may tend to increase flow over the exhalation, and/or may loosen and/or expel secretions with an enhanced effectiveness.

In some embodiments, system 10 includes one or more of subject 12, a user control interface 14, a subject interface 16, one or more sensors 18, a pressure regulator 20, pressure relief valve 25, a controller 22, and/or other components.

User control interface 14 is configured to provide an interface between system 10 and subject 12 through which subject 12 provides information to and receives information from system 10. This enables data, results, and/or instructions and any other communicable items, collectively referred to as "information," to be communicated between subject 12, one or more of subject interface 16, and/or controller 22. Examples of interface devices suitable for inclusion in user control interface 14 include a keypad, buttons, switches, a keyboard, knobs, levers, a display screen, a touch screen, speakers, a microphone, an indicator light, an audible alarm, a printer, a tactile feedback device, a gesture recognition device, and/or other interface devices. For example, in some implementations, subject 12 pushes a button to communicate to controller 22 that pressure is built in subject interface 16. In one embodiment, user control interface 14 includes a plurality of separate interfaces. For example, system 10 may be configured with the push button mentioned above, and/or a gesture (e.g., facial movement such as blinking) recognition device for use by a subject who may not have full physical control of their extremities (e.g., a fully or partially paralyzed subject).

It is to be understood that other communication techniques, either hardwired or wireless, are also contemplated by the present disclosure as user control interface 14. For example, the present disclosure contemplates that user control interface 14 is a remote control. In this example, information indicating a pressurized subject user interface is wirelessly transmitted to controller 22 that enables subject 12 to begin the segmented exsufflation process controlled by system 10. Other exemplary input devices and techniques adapted for use with system 10 as user control interface 14 include, but are not limited to, an RS-232 port, RF link, an IR link, modem (telephone, cable or other). In short, any technique for communicating information with system 10 is contemplated by the present disclosure as user control interface 14.

Subject interface 16 is configured to interface with the airway of subject 12. Subject interface 16 is configured to provide fluid communication with the airway of subject 12. As such, subject interface 16 includes a conduit 24 and/or an interface appliance 26. Conduit 24 conveys gas (e.g., air) to and/or from interface appliance 26, and interface appliance 26 places conduit 24 in communication with the airway of subject 12. In some embodiments, subject interface 16 is non-invasive. As such, interface appliance 26 non-invasively engages subject 12. Non-invasive engagement includes removably engaging an area (or areas) surrounding one or more external orifices of the airway of subject 12 (e.g., nostrils and/or mouth) to communicate gas between the airway of subject 12 and subject interface 16. Some examples of non-invasive interface appliance 26 may include, for example, a blow tube, a nasal cannula, a nasal mask, a nasal/oral mask, a full face mask, a total face mask, or other interface appliances that communicate a flow of gas with an airway of a subject.

Sensors 18 are configured to generate output signals conveying information related to one or more gas parameters of the gas within subject interface 16. The one or more gas parameters comprise flow, volume, pressure, temperature, humidity, velocity, and/or other gas parameters. Gas parameter sensors 18 may comprise one or more sensors that measure such parameters directly (e.g., through fluid communication with the flow of gas in subject interface 16). Gas parameter sensors 18 may comprise one or more sensors that generate output signals related to one or more parameters of the flow of gas indirectly. For example, one or more of sensors 18 may generate an output based on an operating parameter of the pressure regulator 20 (e.g., a valve driver or motor current, voltage, rotational velocity, and/or other operating parameters), and/or other sensors. Although gas parameter sensors 18 are illustrated at a single location within (or in communication with) conduit 24 between interface appliance 26 and pressure regulator 20, this is not intended to be limiting in anyway. Gas parameter sensors 18 may include sensors disposed in a plurality of locations, such as, for example, within pressure regulator 20, within (or in communication with) interface appliance 26, anywhere on subject interface 16, and/or other locations of system 10.

Pressure regulator 20 is configured to selectively control flow through subject interface 16. Pressure regulator 20 is configured to operate in a first mode, a second mode, and/or in other modes. In the first mode, subject interface 16 is closed such that substantially no gas is communicated with the airway of subject 12 therethrough. In the second mode, subject interface 16 is opened to permit gas to be exhausted from the airway of subject 12 through subject interface 16.

In first mode of operation of pressure regulator 20, a closed flow path is formed between interface appliance 26, in fluid communication with airway of subject 12, and pressure regulator 20 through pressure relief valve 25. In second mode of operation of pressure regulator 20, pressure regulator 20 is configured to expose the closed flow path to ambient atmosphere through an exsufflation flow path. The exsufflation flow path is a flow path out of subject interface 16 to ambient atmosphere by pressure regulator 20. The exsufflation flow path allows air to flow out of the lungs of subject 12 during a series of exsufflation events caused over an individual exhalation of subject 12.

In one embodiment, pressure regulator 20 is configured to operate based on inspiratory time and/or inspiratory volume. For example, in one embodiment, pressure regulator 20 is configured to open in response to a longer inspiration time period. In another embodiment, pressure regulator 20 is configured to open in response to a higher inspiratory volume of flow in a shorter period of inspiratory time.

In some implementations, pressure regulator 20 may comprise one or more of a valve and/or another pressure regulating device. In one embodiment, pressure regulator 20 may comprise one or more valves in series and/or in parallel. Examples of valves and/or other pressure regulating devices suitable for inclusion in pressure regulator 20 may include a plug valve, a ball valve, a check valve, a butterfly valve, a solenoid, and/or other pressure regulating devices. The pressure regulating devices mentioned above and/or other pressure regulating devices that may be included in pressure regulator 20 may be controlled hydraulically, pneumatically, via an electric motor and/or another mode of control configured to open and/or close a valve and/or other pressure control device.

In some implementations, pressure regulator 20 may be located at one or more locations in system 10. For example, in one embodiment, pressure regulator 20 may be located at one end of subject interface 16, opposite interface appliance 26. In a second embodiment, pressure regulator 20 may be located between interface appliance 26 and conduit 24.

Pressure relief valve 25 is associated with subject interface 16 and configured to open and release gas out of subject interface 16, responsive to pressure within subject interface 16 exceeding a predetermined threshold value so as to maintain the pressure within subject interface 16 within a predetermined pressure range during the enhanced cough flow.

Pressure relief valve 25 is configured to operate in a closed, seal position and in an open, release position. Pressure relief valve 25 is configured to operate between the open and closed positions when pressure regulator 20 is in its first mode of operation. Specifically, when pressure regulator 20 is in its first mode of operation, pressure relief valve 25 is configured to be in the closed position when pressure in subject interface 16 is at or below a predetermined pressure threshold valve and pressure relief valve 25 is configured to be in the open position when pressure in subject interface 16 is above the predetermined pressure threshold valve. Pressure relief valve 25 is also configured to be in the closed position when pressure regulator 20 is in its second mode of operation.

When pressure regulator 20 is in its first mode of operation and the pressure in the closed flow path (i.e., between interface appliance 26, in fluid communication with airway of subject 12, and pressure regulator 20) is above a predetermined pressure threshold valve, pressure relief valve 25 is configured to open to expose the closed flow path to ambient atmosphere through a secondary flow path. When in its open, release position, pressure relief valve 25 is configured to release gas flowing in the closed flow path into ambient atmosphere via the secondary flow path. Pressure relief valve 25 opens the secondary flow path to ambient atmosphere that is different than any flow path to ambient atmosphere or any flow path out of subject interface 16 by pressure regulator 20. For example, the secondary flow path of pressure relief valve 25 is different from the exsufflation flow path (discussed above) of pressure regulator 20. When in its closed, seal position, pressure relief valve 25 is configured to prevent gas from flowing from the closed flow path into ambient atmosphere via the secondary flow path.

In one embodiment, pressure relief valve 25 is physically separate from pressure regulator 20 and does not share components with pressure regulator 20. In some implementations, pressure relief valve 25 may be located at one or more locations in system 10. For example, in one embodiment, pressure relief valve 25 may be located on subject interface 16 near pressure regulator 20 as shown in FIG. 1. It should be appreciated that pressure relief valve 25 may be located elsewhere on subject interface 16 so long as pressure relief valve 25 is in communication with the gas flowing through subject interface 16. In another embodiment, relief valve 25 is located anywhere on subject interface 16 between interface appliance 26 and pressure regulator 20.

In one embodiment, the predetermined pressure threshold value may include a pressure of 25 measured in centimeter of water (cm $H_2O$). In another embodiment, the predetermined threshold value may include a pressure of 40 cm $H_2O$. In yet another embodiment, the predetermined threshold value may include a pressure of 60 cm $H_2O$. In one embodiment, the predetermined pressure range may be between 20 and 100 cm $H_2O$. In another embodiment, the predetermined pressure range may be between 20 and 60 cm $H_2O$.

The predetermined threshold value or predetermined pressure range may be stored in a memory of system 10. The predetermined threshold value or predetermined pressure range may be configurable to subject 12, predefined at manufacture, determined dynamically based on previous respiration by subject 12, and/or determined in other manners. The predetermined threshold value or predetermined pressure range may be provided and may be changed by subject 12 using user control interface 14. In one embodiment, the predetermined pressure threshold value may be at or below an operational proof pressure of pressure sensor 18. In one embodiment, the predetermined pressure threshold value may be set to a value less than the operational proof pressure of pressure sensor 18 so as to provide a margin for tolerance. This configuration enables pressure relief valve 25 to decrease the pressure within subject interface 16 such that the pressure is below operational proof pressure of pressure sensor 18 to protect the electronics of pressure sensor 18. In another embodiment, when pressure relief valve 25 is configured to operate mechanically (i.e., pressure relief valve 25 is not associated with controller 22 and/or sensor 18 to operate), the predetermined threshold value or predetermined pressure range may be set by manufacturer or may be adjusted by the patient through mechanical adjustment of pressure relief valve 25.

Figure 2:
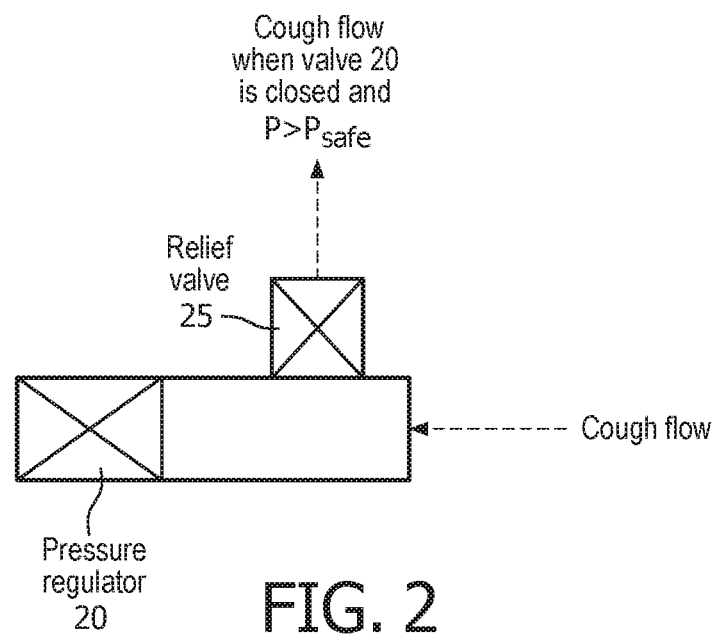
FIG. 2 shows an embodiment of a relief valve of the system, where the relief valve is separate from a pressure regulator of the system.

FIG. 2 shows an embodiment of pressure relief valve 25 being separate from pressure regulator 20 of system 10. Pressure relief valve 25 is connected to pressure regulator 20 by a conduit. When pressure regulator 20 is in its first mode of operation and the pressure in closed flow path is above a predetermined threshold valve, pressure relief valve 25 opens the secondary flow path to ambient atmosphere that is different than any flow path to ambient atmosphere or any flow path out of subject interface 16 by pressure regulator 20.

Figure 3:
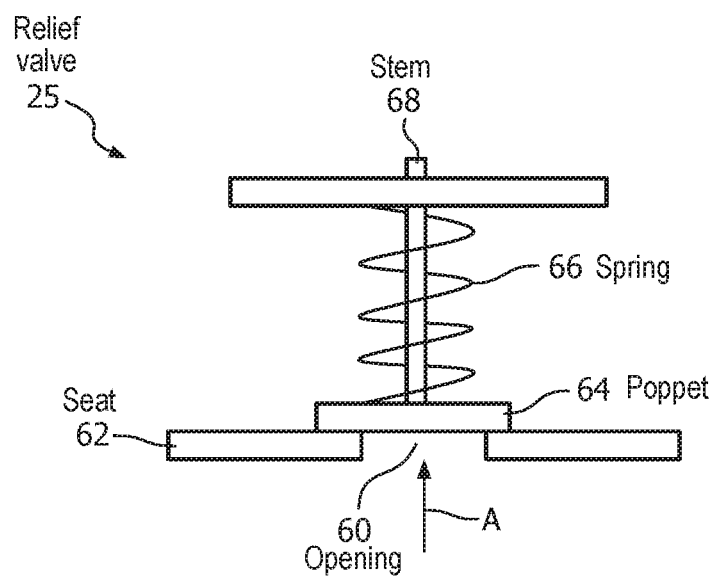
FIG. 3 shows an exemplary embodiment of the relief valve of the system.

FIG. 3 shows an embodiment of pressure relief valve 25 taking the form of a normally closed mechanical poppet valve. Poppet valve 25 may be in a closed position wherein gas is prevented from being passed therethrough and an open position wherein gas is permitted to pass therethrough. Pressure relief valve 25 may include a housing having an opening 60 for gas to flow into pressure relief valve 25, a spring 66 disposed inside housing, a poppet 64 for closing and opening pressure relief valve 25, a stem 68 that is connected to poppet 64, and a seat 62 that contacts poppet 64 when pressure relief valve 25 is in its closed position. Pressure relief valve 25 includes outlets (secondary flow path) for gas to pass therethrough to decrease the pressure inside subject interface 16 when pressure relief valve 25 is in its open position. Spring 66 may normally push poppet 64 in a closed position against seat 62 so as to seal opening 60 of pressure relief valve 25 to prevent gas from flowing into pressure relief valve 25.

The pressure of the gas may push poppet 64 away from seat 62, thus moving pressure relieve valve 25 to its open position. That is, spring 66 is configured to oppose movement of poppet 64 in the direction of A, while the pressure of the gas may push poppet 64 in the direction of A. Seat 62 may be made of elastomeric material that enables poppet 64 to form a seal with seat 62 so as to prevent gas from flowing therein. The characteristics of the spring, such as the spring force and/or elasticity, may be varied according to the desired predetermined threshold pressure at which pressure relief valve 25 may be opened. That is, the desired predetermined threshold at which pressure relief valve 25 may open when the pressure in subject interface 16 exceeds the threshold may be associated with the force of the spring. The force of the spring may be varied based on, for example, Hooke's law.

Pressure relief valve 25 is configured to relieve pressure (open) responsive to the pressure within subject interface 16 exceeding the predetermined threshold value so as to decrease pressure within subject interface 16 when pressure regulator is in its first mode of operation. In the embodiment of pressure relief valve 25 shown in FIG. 3, the pressure may push poppet 64 upwards in the direction of A against the force of spring 66 and away from seat 62, thus enabling gas to flow through opening 60 and into pressure relief valve 25, which may then output the gas into the ambient atmosphere. After the pressure has been sufficiently decreased, spring 66 may bias poppet 64 back against seat 62 so as to close pressure relief valve 25.

It should be appreciated that pressure relief valve 25 may have other configurations or take other forms in other embodiments. Pressure relief valve 25 may be a mechanical valve, but may also be an electronic valve operated by controller 22. For example, pressure relief valve 25 may be a normally closed pilot solenoid valve configured to be opened by controller 22 when controller 22 determines that the pressure within subject interface 16 is above or at the predetermined pressure threshold value. However, it should be appreciated that these examples are not intended to be limiting and pressure relief valve 25 may have other configurations in other embodiments.

Figure 4:
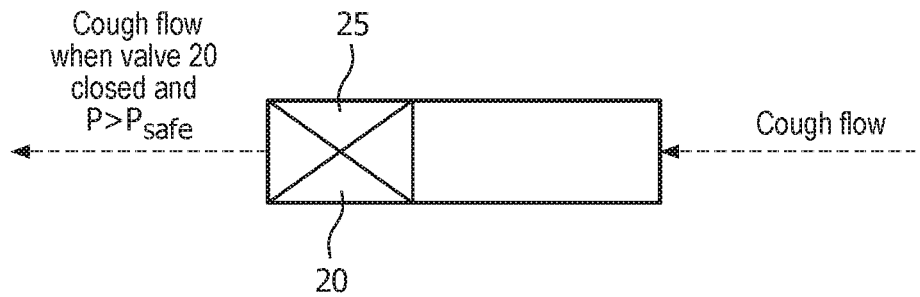
FIG. 4 shows an embodiment of the relief valve of the system, where the relief valve is integrated with the pressure regulator of the system.
Figure 5:
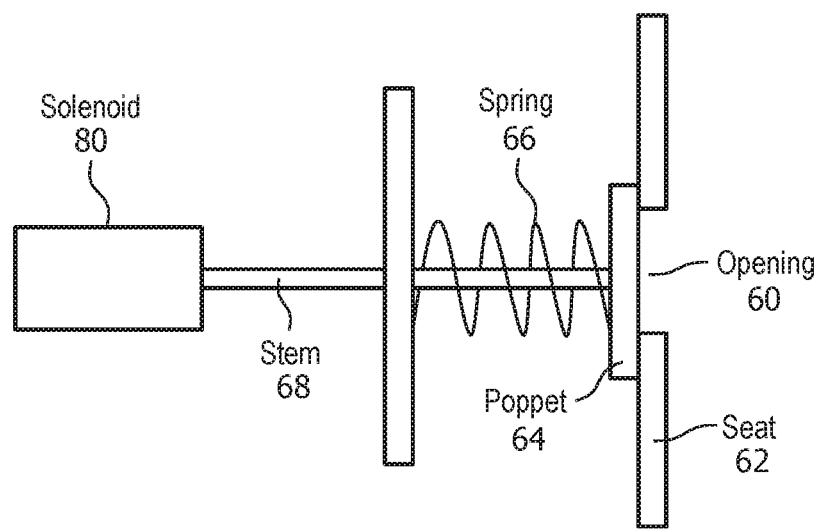
FIG. 5 shows another exemplary embodiment of the relief valve of the system.

For example, FIGS. 4 and 5 show an embodiment of pressure relief valve 25 being integrated with pressure regulator 20 of system 10. The integrated pressure regulator and relief valve system may include two separate ports to ambient atmosphere, and a solenoid 80 controlling the integrated pressure regulator and relief valve system to selectively open and close ports to ambient atmosphere. The first port to ambient atmosphere allows gas to be exhausted from the airway of subject 12 through subject interface 16 during exsufflation of subject 12. The second port to ambient atmosphere releases gas from the airway of subject 12 through subject interface 16 prior to exsufflation of subject 12 so as to relieve pressure within subject interface 16, responsive to the pressure within subject interface 16 exceeding the predetermined threshold value.

When in a non-energized state, solenoid 80 is configured to close the first port to the ambient atmosphere after an exsufflation of subject 12 through subject interface 16. In this position, if it is determined that pressure in subject interface 16 exceeds the predetermined pressure threshold value, solenoid 80 opens the second port to ambient atmosphere to allow gas to be released from the airway of subject 12 through subject interface 16. The solenoid 80 is configured to close the second port to the ambient atmosphere when a cough trigger event is detected. In this position, solenoid 80 opens the first port to ambient atmosphere to allow gas to be exhausted from the airway of subject 12 through subject interface 16 during exsufflation of subject 12.

Referring back to FIG. 1, controller 22 is configured to provide information processing capabilities in system 10. As such, controller 22 may include one or more of a digital processor, an analog processor, a digital circuit designed to process information, an analog circuit designed to process information, a state machine, and/or other mechanisms for electronically processing information. Although controller 22 is shown in FIG. 1 as a single entity, this is for illustrative purposes only. In some implementations, controller 22 includes a plurality of processing units. These processing units may be physically located within the same device, or controller 22 may represent processing functionality of a plurality of devices operating in coordination. In some implementations, communication between controllers and/or sensor(s) 18 occurs wirelessly or via wires.

As is shown in FIG. 1, controller 22 may be configured to execute one or more computer program modules. The one or more computer program modules comprise one or more of a pressurization module 28, a cough initiation module 30, a cough conclusion module 31, a control module 32, a pressure regulation module 33 and/or other modules. Controller 22 may be configured to execute modules 28, 30, 31, 32 and/or 33 by software; hardware; firmware; some combination of software, hardware, and/or firmware; and/or other mechanisms for configuring processing capabilities on controller 22.

It should be appreciated that although modules 28, 30, 31, 32 and 33 are illustrated in FIG. 1 as being co-located within a single processing unit, in implementations in which controller 22 includes multiple processing units, one or more of modules 28, 30, 31, 32 and/or 33 may be located remotely from the other modules. The description of the functionality provided by the different modules 28, 30, 31, 32 and/or 33 described below is for illustrative purposes, and is not intended to be limiting, as any of modules 28, 30, 31, 32 and/or 33 may provide more or less functionality than is described. For example, one or more of modules 28, 30, 31, 32 and/or 33 may be eliminated, and some or all of its functionality may be provided by other ones of modules 28, 30, 31, 32 and/or 33. As another example, controller 22 may be configured to execute one or more additional modules that may perform some or all of the functionality attributed below to one of modules 28, 30, 31, 32 and/or 33.

Pressurization module 28 is configured to receive information indicating whether respiratory effort of subject 12 (e.g., unassisted respiratory effort) has pressurized subject interface 16. Based on the received information, pressurization module 28 determines whether subject interface 16 is pressurized. In some embodiments, pressurization module 28 is configured such that the information indicating whether subject 12 has pressurized subject interface 16 comprises an input by subject 12 to user control interface 14. For example, subject 12 pressurizes subject interface 16 by blowing on interface appliance 26 with pressure regulator 20 in the first mode (closed). After pressurization, subject 12 pushes a button of user control interface 14 (or otherwise engages some element of user control interface 14) to indicate that pressure is built in subject interface 16.

In some embodiments, pressurization module 28 is configured such that the information indicating whether the user has pressurized subject interface 16 comprises the output signals of sensors 18. For example, subject 12 pressurizes subject interface 16 by blowing on interface appliance 26 with pressure regulator 20 in the first mode (closed). In such embodiments, pressurization module 28 determines whether subject interface 16 is appropriately pressurized based on the one or more gas parameters for which information is conveyed by the output signals. For example, responsive to a level of a gas parameter breaching a threshold level, pressurization module 28 determines that subject interface 16 is pressurized. Cough initiation module 30 is configured to detect a cough trigger event during normal breathing of subject 12 through subject interface 16. In one embodiment, cough initiation module 30 is also configured to detect a cough trigger event with onset of cough effort when pressure regulator 20 in closed. This breathing occurs while pressure regulator 20 is operating in the second mode so that subject 12 can inhale and exhale freely through subject interface 16. In some embodiments the information indicating a cough trigger event comprises one or more gas parameters (e.g. pressure, flow, and/or other gas parameters) concerning which information is conveyed by the output signals of sensors 18.

A cough trigger event may comprise output signals that indicate an inhalation in preparation for a cough by subject 12. Such an inhalation may be referred to as a preparatory inhalation. A preparatory inhalation may be distinguished from other inhalations of subject 12 through subject interface 16 in that a preparatory inhalation may be sharper (e.g., with a higher magnitude flow rate or a lower pressure) and/or deeper (e.g., with a higher volume of flow) than other inhalations by subject 12. In one embodiment, the preparatory inhalation may have a higher volume of flow in a shorter period of time than other inhalations by subject 12. In another embodiment, the preparatory inhalation may have a longer period of inhalation time than other inhalations by subject 12. In some embodiments, cough initiation module 30 is configured to detect a cough trigger event based on one or more gas parameters breaching a threshold level (e.g., pressure and/or flow breaching threshold(s)). The threshold levels may be configurable to a user (e.g., subject 12, a doctor, a caregiver, a researcher, and/or other users), predefined at manufacture, determined dynamically based on previous respiration by subject 12, and/or determined in other manners.

Cough conclusion module 31 is configured to detect cough conclusion after exsufflation of subject 12 through subject interface 16. Detection of a cough conclusion is made based on input received from subject 12 (e.g., input via user control interface 14 indicating the user is done with the cough), based on the output signals of sensor 18, and/or based on other parameters. Detecting a cough conclusion based on the output signals of sensor 18 may be made by monitoring the output signals for an indication of changes to one or more gas parameters within subject interface 16 indicating that the cough is concluding or has concluded (e.g., that the air in the lungs of subject 12 has been depleted). This may include monitoring one or more of pressure, flow rate, volume and/or other parameters over individual exsufflation events and/or groups of exsufflation events (e.g., for the entire cough, over a sliding window of n most recent events, etc.).

By way of non-limiting example, a cough conclusion may be detected based on a total exhaled volume over the span of the cough. Responsive to the total exhaled volume reaching a threshold amount, the cough conclusion may be detected. The threshold amount may be determined based on an inhaled volume in the inhalation prior to the cough, a user configurable setting, previous coughs by subject 12, and/or determined in other ways.

As another non-limiting example, one or more of pressure, flow rate, and/or volume of individual exsufflation events are monitored to detect a cough conclusion. Responsive to one or more of these parameters breaching a threshold level during an exsufflation event, the cough conclusion may be detected (e.g., not reaching a minimum pressure level, not reaching a minimum flow rate magnitude, not reaching a minimum volume, etc.). In some embodiments, a sliding window of n exsufflation events may be monitored, rather than an individual exsufflation event. In such embodiments, an aggregation (e.g., a sum, an average, a weighted average, etc.) of measurements taken during the individual exsufflation events within the sliding window are compared with a corresponding threshold level. The thresholds may be determined based on a user-configurable setting, based on previous respiration by subject 12 through subject interface 16, predetermined at manufacture, and/or determined in other ways.

As yet another non-limiting example, detection of a cough conclusion is made based on the passage of time. At some time amount after a cough trigger event, and/or a first exsufflation event the cough conclusion may be detected. The time amount may be determined based on a user-configurable setting, based on previous respiration by subject 12 through subject interface 16, predetermined at manufacture, and/or determined in other ways.

Control module 32 is configured to control operation of pressure regulator 20 between the first mode (closed) and the second mode (open) to exsufflate subject 12. Exsufflation is a forced release of gas from the lungs of subject 12. Control module 32 is configured to exsufflate subject 12 by placing pressure regulator 20 in the second (open) mode until a determination by cough initiation module 30 that subject 12 has experienced a cough trigger event. Responsive to such a determination, control module 32 is configured to place pressure regulator 20 in the first mode. As pressure regulator 20 is being operated in the first mode, respiratory effort by subject 12 into subject interface 16 pressurizes subject interface 16. This pressurization is monitored by pressurization module 28 as described above. Responsive to a determination by pressurization module 28 that subject 12 has pressurized subject interface 16 sufficient for a cough, control module 32 is configured to cause a series of segmented exsufflation events over an individual exhalation of subject 12. This exsufflation occurs through subject interface 16. The exsufflation events are created by toggling pressure regulator 20 between the first mode and the second mode during the individual exhalation. Responsive to a determination by cough conclusion module 31 that the cough has concluded, control module 32 is configured to place pressure regulator 20 in the second (open) mode and subject 12 may return to normal breathing.

Pressure regulation module 33 is configured to control operation of pressure relief valve 25 to selectively release gas out of subject interface 16 when pressure regulator 20 is in the first mode. Pressure regulation module 33 controls operation of pressure relief valve 25 between an open position when pressure within subject interface 16 exceeds the predetermined threshold value and a closed position when pressure within subject interface 16 is below the predetermined threshold value. Pressure regulation module 33 is configured to maintain pressure relief valve 25 in the closed position until a determination by sensor 18 that pressure within subject interface 16 exceeds the predetermined threshold value. Responsive to such a determination, pressure regulation module 33 is configured to place pressure relief valve 25 in the release/open position. As pressure relief valve 25 is being operated in the open position, gas within subject interface 16 is released into the ambient atmosphere. Responsive to a determination by sensor 18 that the pressure within subject interface 16 is at or below the predetermined threshold value, pressure regulation module 33 is configured to place pressure relief valve 25 in the closed position and allow subject interface 16 pressurize for a cough. Thus, the pressure within subject interface 16 is relieved by toggling pressure relief valve 25 between the closed and open positions as required when pressure regulator 20 is in the first mode.

In another embodiment, control module 32 may be configured to operate both pressure regulator 20 and pressure relief valve 25. In such an embodiment, system 10 does not include a separate pressure regulation module. In yet another embodiment, pressure relieve valve 25 is a mechanical valve that is configured to operate without any input from control module 32 and/or pressure regulation module 33.

Figure 6:
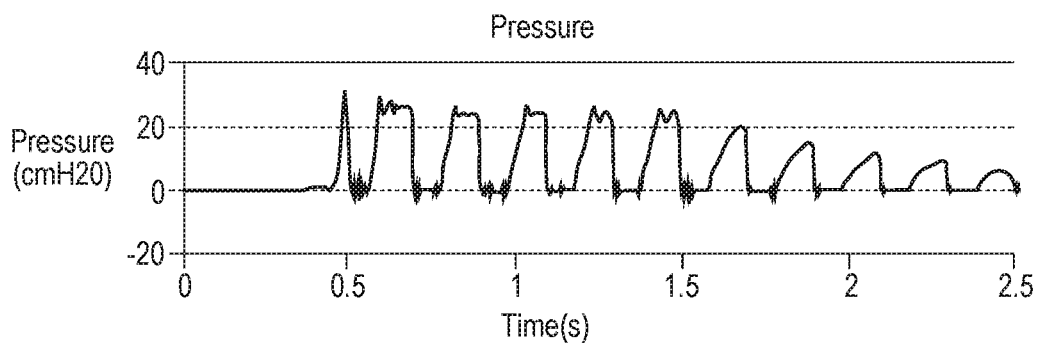
FIG. 6 is a graphical illustration of pressure measurements during enhanced cough flow of the subject using the system with the relief valve.

By way of illustration, FIG. 6 shows a graphical representation of pressure measurements within subject interface 16 during enhanced cough flow of subject 12 using system 10 with pressure relief valve 25. The X-axis represents time measured in seconds and the Y-axis represents pressure within subject interface 16 measured in cm $H_2O$. The predetermined threshold value was set at 25 cm $H_2O$. Without pressure relief valve 25, pressure within subject interface 16 may rise uncontrolled and may easily exceed 100 cm $H_2O$. However, as can be clearly seen from the graph of FIG. 6, pressure relief valve 25 moves between its open and closed positions to maintain pressure within subject interface 16 at or around predetermined threshold value of 25 cm $H_2O$.

Returning to FIG. 1, control module 32 controls one or more parameters of the exsufflation events in a segmented exsufflation. The one or more exsufflation parameters may include, for an individual exsufflation event, one or more of time in the first mode, time in the second mode, a transition from the first mode to the second mode (e.g., the timing of the transition), a transition from the second mode to the first mode (e.g., the timing of the transition), and/or other parameters. In one embodiment, control module 32 is configured such that the transitions from first mode to second mode and/or the transitions from second mode to first mode are initiated based on predetermined timings. The predetermined timings may be based on a period frequency or period length, a standard length for the first mode, a standard length for the second mode, and/or other periodic timings. The predetermined timings may vary over the exhalation (e.g., longer exsufflation events at the beginning of the exhalation and shorter exsufflation events at the end of the exhalation). These timings may be configurable to a user (e.g., subject 12, a caregiver, a researcher, and/or other users). For example one or more user settings may be configurable to users via user control interface 14 to set such timings.

In one embodiment, control module 32 is configured such that the transitions from first mode to second mode and/or transitions from second mode to first mode are initiated based on the output signals generated by sensor 18. For example, subsequent to an initial exsufflation event, control module 32 may be configured to place pressure regulator 20 in the first mode of operation, thereby closing subject interface 16. Pressure regulator 20 may remain in the first mode of operation until respiratory effort by subject 12 against the closure of subject interface 14 causes one or more gas parameters to breach a threshold level (e.g., pressure to rise above a breach pressure threshold). In one embodiment, the breach pressure threshold is 1 cm $H_2O$. In another embodiment, the breach pressure threshold is 2 cm $H_2O$. In yet another embodiment, the breach pressure threshold is 5 cm $H_2O$. In yet another embodiment, the breach pressure threshold range is between 1 and 6 cm $H_2O$. In yet another embodiment, the breach pressure threshold range is less than 10 cm $H_2O$.

Responsive to this, control module 32 may initiate a next exsufflation event by switching pressure regulator 20 from the first mode to the second mode of operation. As another example, while pressure regulator 20 is being operated in the second mode, control module 30 may switch such operation to the first mode responsive to the output signals of sensor 18 indicating that one or more gas parameters have breached a threshold level (e.g., pressure and/or flow falling below threshold(s)). The threshold levels may be may be configurable to a user (e.g., subject 12, a caregiver, a researcher, and/or other users). For example one or more user settings may be configurable to users via user control interface 14 to set such thresholds.

It will be appreciated that the description of the operation of pressure regulator 20 by electronic controller 22 and/or its modules 28, 30, 32 is not intended to be limiting. Other controllers for opening pressure regulator 20 responsive to pressurization of subject interface 16, and/or toggling pressure regulator 20 between the first mode and the second mode to cause a plurality of exsufflation events over an individual exhalation fall within the scope of this disclosure. For example, one or more resilient members (e.g., a spring, a band, and/or other resilient members) (not shown) may operate to cause oscillation of pressure regulator 20 between the first mode and the second mode during the individual exhalation (e.g., the period of time during which gas is exhausted from the lungs of subject 12 without intervening inhalation). Other mechanical controllers are also contemplated.

Figure 7:
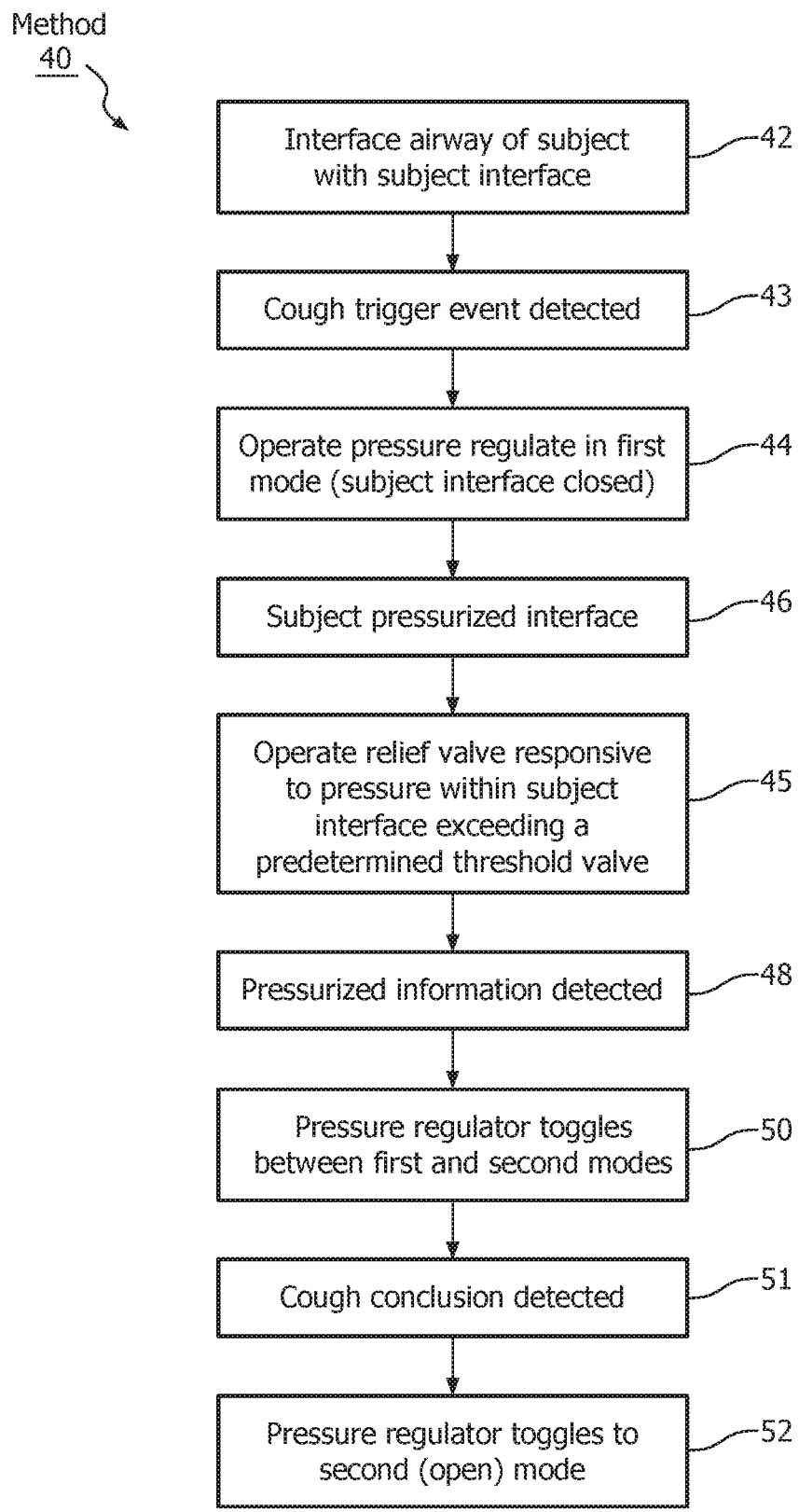
FIG. 7 is a flow chart for illustrating a method to control pressure during enhanced cough flow of the subject.

FIG. 7 illustrates a method 40 of monitoring and controlling pressure during enhanced cough flow of a subject. The operations of method 40 presented below are intended to be illustrative. In some embodiments, method 40 may be accomplished with one or more additional operations not described, and/or without one or more of the operations discussed. Additionally, the order in which the operations of method 40 are illustrated in FIG. 7 and described below is not intended to be limiting.

In some embodiments, method 40 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 40 in response to instructions stored electronically on an electronic storage medium. The one or more processing devices may include one or more devices configured through hardware, firmware, and/or software to be specifically designed for execution of one or more of the operations of method 40.

At an operation 42, a subject interface interfaces with the airway of a subject. In some embodiments, operation 42 is performed by a subject interface and/or an interface appliance the same as or similar to subject interface 16 and/or interface appliance 26 (shown in FIG. 1 and described herein).

At an operation 43, information indicating a cough trigger event is detected. In some embodiments, operation 43 is performed by a controller the same as or similar to controller 22, (shown in FIG. 1 and described herein.)

At an operation 44, a pressure regulator operates in a first mode. In the first mode, subject interface 16 is closed. In some embodiments, operation 44 is performed by a pressure regulator the same as or similar to pressure regulator 20 (shown in FIG. 1 and described herein).

At an operation 45, a pressure relief valve operates to release gas out of subject interface 16, responsive to pressure within subject interface 16 exceeding a predetermined threshold value so as to maintain the pressure within subject interface 16 within a predetermined pressure range during the enhanced cough flow. Pressure relief valve 25 operates when pressure regulator 20 is in the first mode. In some embodiments, operation 45 is performed by a pressure relief valve the same as or similar to pressure relief valve 25 (shown in FIG. 1 and described herein).

At an operation 46, subject interface 16 is pressurized by subject 12. Subject 12 pressurizes subject interface 16 by exerting air pressure on subject interface 16. In some embodiments, operation 46 is performed by a subject interface the same as or similar to subject interface 16 (shown in FIG. 1 and described herein.)

At an operation 48, information indicating pressurization of subject interface 16 by subject 12 is detected. In some embodiments, operation 48 is performed by a controller the same as or similar to controller 22, (shown in FIG. 1 and described herein).

At an operation 50, the pressure regulator toggles between the first closed mode and a second open mode. In the second mode, subject interface 16 is opened to permit gas to be exhausted from the airway of subject 12. Toggling between the first and second modes exsufflates subject 12 with a series of segmented exsufflation events during a single exhalation. In some embodiments, operation 50 is performed by a pressure regulator the same as or similar to pressure regulator 20, (shown in FIG. 1 and described herein).

At an operation 51, information indicating cough conclusion is detected. In some embodiments, operation 51 is performed by a controller the same as or similar to controller 22, (shown in FIG. 1 and described herein).

At an operation 52, the pressure regulator toggles to the second (open) mode. In some embodiments, operation 52 is performed by a pressure regulator the same as or similar to pressure regulator 20, (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to control pressure during enhanced cough flow of a subject, the system comprising:
    a subject interface configured to communicate with an airway of the subject;
    a pressure regulator comprising a first valve configured to selectively control flow through the subject interface, the pressure regulator operating in (i) a first mode in which the subject interface is closed such that substantially no gas is communicated with the airway of the subject therethrough, and (ii) a second mode in which the subject interface is opened to permit gas to be exhausted from the airway of the subject through the subject interface;
    a controller configured to operate the pressure regulator such that during an individual exhalation of the subject, the pressure regulator is toggled between the first mode and the second mode to cause a series of exsufflation events for the individual exhalation of the subject; and
    a pressure relief valve that is separate from the first valve and associated with the subject interface and configured to:
        open and release gas out of the subject interface responsive to pressure within the subject interface exceeding a predetermined threshold value while the pressure regulator operates in the first mode; and
        remain closed while the pressure regulator operates in the second mode, so as to maintain the pressure within the subject interface within a desired range during the enhanced cough flow.

2. The system of claim 1, wherein the pressure relief valve comprises a poppet and spring configured to operate responsive to the pressure within the subject interface exceeding the predetermined threshold value.

3. The system of claim 1, wherein the pressure relief valve comprises a solenoid valve configured to operate responsive to the pressure within the subject interface exceeding the predetermined threshold value.

4. The system of claim 1, further comprising a sensor in fluid communication with the gas flowing through the subject interface and configured to generate an output signal conveying information related to the pressure within the subject interface.

5. The system of claim 4, wherein the sensor is disposed between the pressure regulator and the pressure relief valve.

6. The system of claim 5, further comprising a pressure regulation module configured to operate the pressure relief valve to:
    open and release gas out of the subject interface responsive to a determination by the sensor that the pressure within the subject interface exceeding the predetermined threshold value while the pressure regulator operates in the first mode; and
    remain closed until the determination by the sensor that the pressure within the subject interface exceeds the predetermined threshold value while the pressure regulator operates in the second mode, so as to maintain the pressure within the subject interface within the desired range during the enhanced cough flow.

7. The system of claim 1, wherein, in the first mode of the pressure regulator, a closed flow path is formed between an interface appliance that communicates with the airway of the subject and the pressure regulator through the pressure relief valve,
    wherein, in the second mode of the pressure regulator, the pressure regulator is configured to expose the closed flow path to ambient atmosphere through an exsufflation flow path out of the subject interface to ambient atmosphere by the pressure regulator,
    wherein, when the pressure regulator is in the first mode and the pressure in the closed flow path is above the predetermined threshold valve, the pressure relief valve is configured to open to expose the closed flow path to the ambient atmosphere through a secondary flow path, and
    wherein the secondary flow path of the pressure relief valve is different from the exsufflation flow path of the pressure regulator.

8. A method for controlling a cough flow system to control pressure during enhanced cough flow of a subject, the method comprising:
    interfacing with an airway of the subject with a subject interface;
    operating, via a controller, a pressure regulator comprising a first valve in a first mode in which the subject interface is closed such that substantially no gas is communicated with the airway of the subject therethrough;
    operating a pressure relief valve that is separate from the first valve to open and release gas out of the subject interface responsive to pressure within the subject interface exceeding a predetermined threshold value while the pressure regulator operates in the first mode, so as to maintain the pressure within the subject interface within a desired range during the enhanced cough flow;
    receiving information indicating pressurization of the subject interface by the subject; and
    exsufflating the subject with a series of exsufflation events by toggling the pressure regulator between the first mode and a second mode to create the series of exsufflation events during a single exhalation, wherein in the second mode the subject interface is opened to permit gas to be exhausted from the airway of the subject through the subject interface and the pressure relief valve remains closed.

9. The method of claim 8, wherein the pressure relief valve comprises a poppet and spring configured to operate responsive to the pressure within the subject interface exceeding the predetermined threshold value.

10. The method of claim 8, wherein the pressure relief valve comprises a solenoid valve configured to open responsive to the pressure within the subject interface exceeding the predetermined threshold value.

11. The method of claim 8, further comprising generating an output signal conveying information related to the pressure within the subject interface using a sensor in fluid communication with the gas flowing through the subject interface.

12. A system configured to control pressure during enhanced cough flow of a subject, the system comprising:
means for interfacing with an airway of the subject;
means for selectively controlling flow through the means for interfacing, the means for selectively controlling flow comprising a first valve, the means for selectively controlling flow operating in (i) a first mode in which the means for interfacing is closed such that substantially no gas is communicated with the airway of the subject therethrough, and (ii) a second mode in which the means for interfacing is opened to permit gas to be exhausted from the airway of the subject through the means for interfacing;
means for maintaining pressure within the means for interfacing within a desired range that is separate from the first valve, the means for maintaining opening and releasing gas out of the means for interfacing responsive to the pressure within the means for interfacing exceeding a predetermined threshold value while the means for selectively controlling flow operates in the first mode, the means for maintaining remaining closed while the means for selectively controlling operates in the second mode;
means for receiving information indicating whether the subject has pressurized the means for interfacing; and
means for controlling operation of the means for selectively controlling flow such that during an individual exhalation of the subject, the means for selectively controlling flow is toggled between the first mode and the second mode to cause a series of exsufflation events for the individual exhalation of the subject.

13. The system of claim 12, wherein the means for maintaining the pressure comprises a poppet and a spring configured to operate responsive to the pressure within the means for interfacing exceeding the predetermined threshold value.

14. The system of claim 12, wherein the means for maintaining the pressure comprises a solenoid valve configured to operate responsive to the pressure within the means for interfacing exceeding the predetermined threshold value.

15. The system of claim 12, further comprising a means for generating an output signal conveying information related to the pressure within the means for interfacing, the means for generating in fluid communication with the gas flowing through the means for interfacing.

16. The system of claim 12, wherein the means for selectively controlling flow is configured to operate based on inspiratory time and/or inspiratory volume.

* * * * *